United States Patent [19]

Murphy

[11] Patent Number: 5,763,887
[45] Date of Patent: Jun. 9, 1998

[54] TAILORED OPTICAL INTERFACE FOR SCINTILLATION CAMERA DETECTOR

[75] Inventor: Matthew J. Murphy, Los Altos, Calif.

[73] Assignee: ADAC Laboratories, Milpitas, Calif.

[21] Appl. No.: 691,585

[22] Filed: Aug. 2, 1996

Related U.S. Application Data

[60] Provisional application No. 60/001,905, Aug. 4, 1995.

[51] Int. Cl.⁶ .................... G01T 1/164; G01T 1/20
[52] U.S. Cl. ............................. 250/366; 250/368
[58] Field of Search ........................... 250/366, 368

[56] References Cited

U.S. PATENT DOCUMENTS

| | | | |
|---|---|---|---|
| 3,814,938 | 6/1974 | Martone et al. | 250/366 |
| 4,187,427 | 2/1980 | Cusano | 250/366 |
| 4,284,891 | 8/1981 | Pergrale et al. | 250/363 |
| 4,532,425 | 7/1985 | Abileah et al. | 250/368 |
| 4,658,141 | 4/1987 | Wilt et al. | 250/361 R |
| 5,616,924 | 4/1997 | Petrillo | 250/368 |

OTHER PUBLICATIONS

Laser Focus World, Jun. 1996, High–Power transmission grating, p. 148.
Polaroid Imagix™ Holographic Reflectors advertisement, (date unknown).

*Primary Examiner*—Don Wong
*Attorney, Agent, or Firm*—Blakely, Sokoloff, Taylor & Zafman LLP

[57] ABSTRACT

A scintillation camera detector head comprises a scintillation crystal, a plurality of photomultiplier tubes (PMTs) optically coupled to the scintillation crystal, and a diffractive surface, such as a holographic optical element (HOE), optically coupled to the scintillation crystal. The diffractive surface preferentially reflects or redirects light from a scintillation event which impinges upon the surface toward one or more predetermined PMTs as a function of the angle of incidence or the location of the event. Light emitted under a peak PMT can be preferentially reflected or transmitted away from the peak PMT and toward the surrounding PMTs to reduce spatial resolution modulation. Alternatively, light impinging on the surface from an event can be directed toward the peak PMT and away from surrounding PMTs to achieve greater isolation of events.

49 Claims, 11 Drawing Sheets

TAILORED OPTICAL INTERFACE FOR SCINTILLATION CAMERA DETECTOR

This application claims the benefit under 35 U.S.C. § 119(e) of U.S. Provisional Patent Application No. 60/001,905, filed on Aug. 4, 1995.

FIELD OF THE INVENTION

The present invention pertains to the field of scintillation camera imaging. More particularly, the present invention relates to a tailored optical interface for a scintillation camera.

BACKGROUND OF THE INVENTION

Scintillation cameras, sometimes referred to as "gamma cameras", have been used for medical diagnostic imaging for many years. Scintillation camera imaging relies on a scintillation crystal, which emits pulses of light when exposed to ionizing gamma radiation. In a scintillation camera, the scintillation crystal is optically coupled to an array of photomultiplier tubes (PMTs), which detect the emitted light pulses and convert them into electrical signals. The electrical signals are decoded by circuitry which computes position coordinates for each detected light pulse. An image is created for display on a monitor, such as a cathode ray tube (CRT), based on the computed light distribution from the scintillations occurring within the crystal.

During scintillation, photons emitted from a point within the crystal are emitted in all directions, including back toward the bottom surface of the crystal (i.e., away from the PMTs). Consequently, the surface of the crystal opposite from the PMTs is generally covered with a reflective coating or paper to increase the amount of light gathered by the PMTs. The properties of this coating or paper are tailored so that light is reflected back toward the PMTs in a manner which improves the positioning properties of the entire crystal sandwich. One approach to reflectance tailoring causes any light hitting the surface to be reflected at the same angle as the angle of incidence. This property is called "specular" reflection. Another form of reflectance tailoring is called "diffuse" reflection. In diffuse reflection, light impinging on the surface has equal probability of being reflected in all angles. Diffuse reflection is often used in scintillation cameras. The diffuse reflector surface increases the total light detected by those PMTs which are close to the gamma scintillation location.

Scintillation cameras which use diffuse reflection surfaces, however, tend to be susceptible to inaccuracies in the calculation of position information. These inaccuracies affect the quality of the spatial resolution of the camera. In particular, the accuracy of the position information tends to vary depending upon the actual location of the scintillation event relative to the PMTs. Generally, the accuracy of the positioning information is best when the scintillation event occurs between PMTs (where there are double and triple intersection points) and worst when the scintillation occurs directly under a PMT. This variance in accuracy is caused by the relative percentages of light distributed among the PMTs. The light distribution seen at an intersection of two or more PMTs is almost equal between the nearest PMTs.

This distribution yields a favorable signal-to-noise ratio in those PMTs.

However, when the scintillation occurs directly under a PMT (the "peak PMT"), approximately 50% of the light is seen by that PMT, while the remainder of the light is distributed equally among the other PMTs. Consequently, the peak PMT receives excess light, while the other PMTs are starved for light. This phenomenon causes a spatial resolution "modulation" over the entire surface of the detector, i.e., variances in the spatial resolution as a function of physical coordinates. Hence, it would be desirable to provide a scintillation camera having a reflective surface tailored to reduce spatial resolution modulation.

Two medical imaging techniques which use gamma cameras are single photon emission computed tomography (SPECT) and positron emission tomography (PET). In the past, gamma camera systems have been designed to perform either SPECT or PET, but not both. One reason that is the case, is that scintillation materials used for SPECT generally were not suitable for PET. Thallium-activated sodium iodide NaI(Tl) crystal is commonly used in SPECT. However, PET generally required scintillators with a greater stopping power and shorter scintillation decay time than NaI, such as bismuth germanate (BGO) or gadolinium orthosilicate (GSO). Hence, it was not economically feasible to produce a dual SPECT/PET system. ADAC Laboratories, Inc., of Milpitas, California, however, has developed a cost-effective, dual-mode gamma camera system that is capable of performing both SPECT and PET. This system has adapted NaI-based detectors for use in both SPECT and PET.

Some scintillation materials associated with PET do have certain advantages over NaI, however. For example, such materials can be configured as "block detectors". A block detector is characterized by a number of cuts, or slices, made partially through the thickness of the scintillation crystal in a direction perpendicular to the crystal's imaging surface. The cuts generally form a checkerboard pattern in the imaging surface. Each of these cuts acts as a light barrier, so that light rays from a given scintillation event are confined within a very small area of the crystal defined by intersecting cuts. Such isolation of scintillation events is advantageous, in that a large number of events can be processed in parallel with little ambiguity in position determination. Unlike PET scintillators, however, the properties of NaI make it impractical to configure NaI crystals in the form of block detectors. In particular, NaI is hygroscopic, making the crystal fragile and difficult to manipulate. Therefore, it would be desirable to obtain some of the beneficial light transmission characteristics associated with a block detector in an NaI-based detector.

In addition, scintillation crystals used for SPECT are generally thicker than those used for PET. Generally, the stopping power for a given scintillation material increases as thickness is increased. The advantage of greater stopping power is higher collection efficiency, which allows shorter imaging sessions. However, as thickness increases, spatial resolution generally decreases. The reason for this property is that, in a crystal of a given thickness, light emitted from certain scintillation events disperses over a wider area before reaching the PMTs, than it would in a thinner crystal. Hence, it would be desirable to obtain a better trade-off between stopping power and spatial resolution in a given scintillation detector.

One practical application in which the design trade-offs between various detectors are of particular interest is in a dual SPECT/PET system. In such a system, and in others, it would be particularly desirable to provide some of the advantageous light transmission characteristics of a block detector in a continuous crystal detector. It would further be desirable to achieve improved spatial resolution and to achieve a better trade-off between collection efficiency and spatial resolution.

SUMMARY OF THE INVENTION

A scintillation detector comprises a scintillator, a number of light detectors optically coupled to the scintillator, and an optical interface optically coupled to the scintillator. Light emitted from a location within the scintillator which impinges on the optical interface is preferentially directed toward one or more predetermined light detectors based on the location at which the light impinged on the interface.

Other features of the present invention will be apparent from the accompanying drawings and from the detailed description which follows.

BRIEF DESCRIPTION OF THE DRAWINGS

The present invention is illustrated by way of example and not limitation in the figures of the accompanying drawings, in which like references indicate similar elements and in which.

DETAILED DESCRIPTION

A method and apparatus for reducing spatial resolution modulation in a scintillation camera is described. In the following description, for purposes of explanation, numerous specific details are set forth in order to provide a thorough understanding of the present invention. It will be evident, however, to one skilled in the art that the present invention may be practiced without these specific details. In other instances, well-known structures and devices are shown in block diagram form in order to avoid unnecessarily obscuring the present invention.

As will be discussed below, the present invention includes a tailored optical interface which can be used to reduce spatial resolution modulation and to otherwise improve the optical characteristics of a gamma camera detector. The optical interface has properties which cause it to preferentially reflect and/or transmit light from a scintillation event in a designed way.

Figure 1:
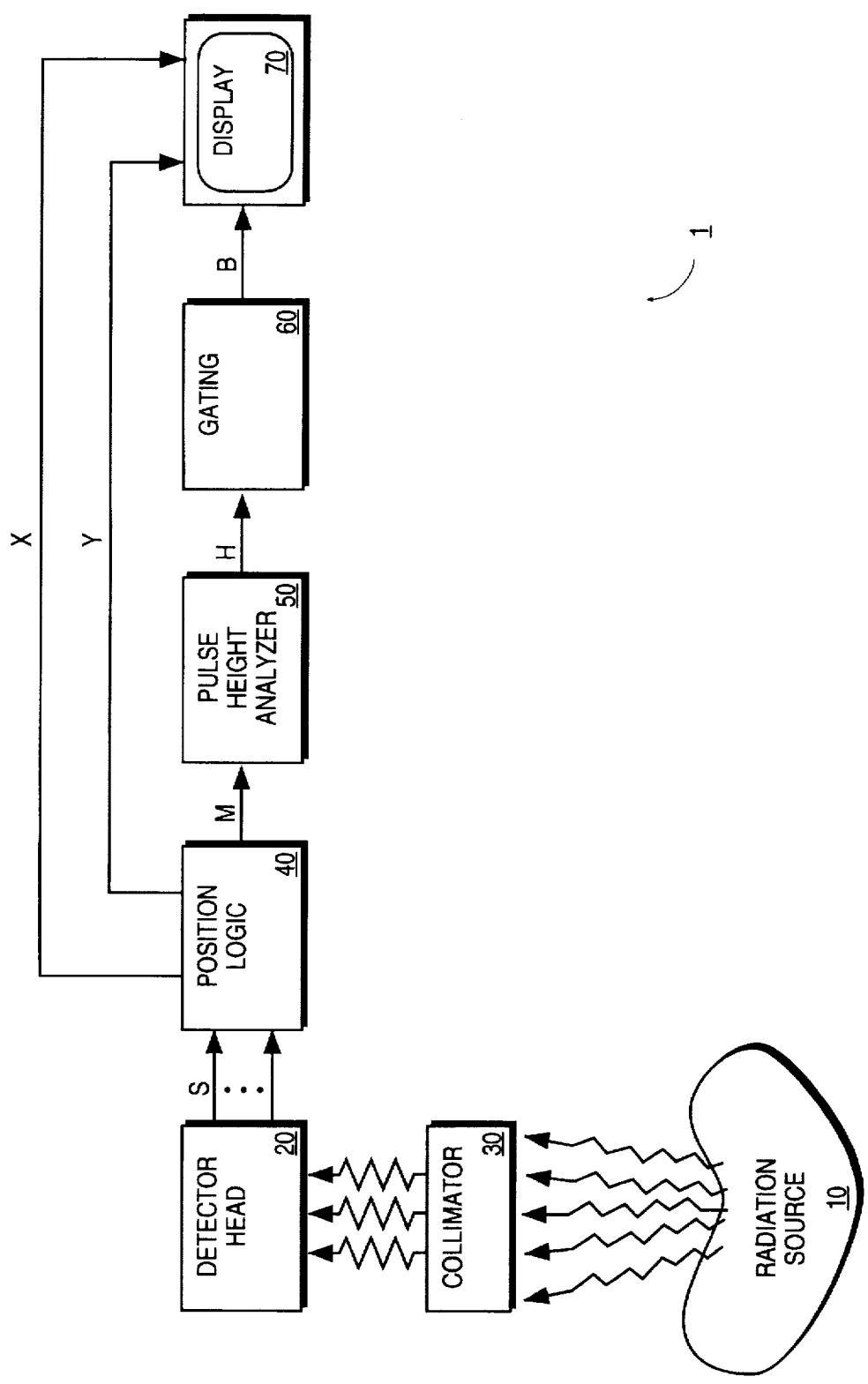
FIG. 1 is a block diagram of a gamma camera imaging system.

FIG. 1 illustrates a nuclear medicine imaging system 1 in which the present invention can be implemented. The system 1 comprises a scintillation detector head 20, a collimator 30, position logic 40, a pulse height analyzer 50, a gating circuit 60, and a display 70. Note that, while the collimator 30 generally would be used during SPECT data acquisition, it would generally not be used during PET data acquisition. During an imaging session, gamma radiation emitted from a radiation source 10 impinges on the detector head 20 (after passing through the collimator 30, in the case of SPECT). The detector head 20 outputs signals S to positioning logic 40 in response to gamma radiation-induced scintillations occurring within the detector head 20. The positioning logic 40 decodes the signals S to provide magnitude information M to the pulse height analyzer 50 and positioning signals X and Y to the display 70. The gating circuit 60 receives an output H of the pulse height analyzer 50 and provides in response a blanking signal B to the display 70. The display 70 provides an image of the radiation source 10.

Figure 2:
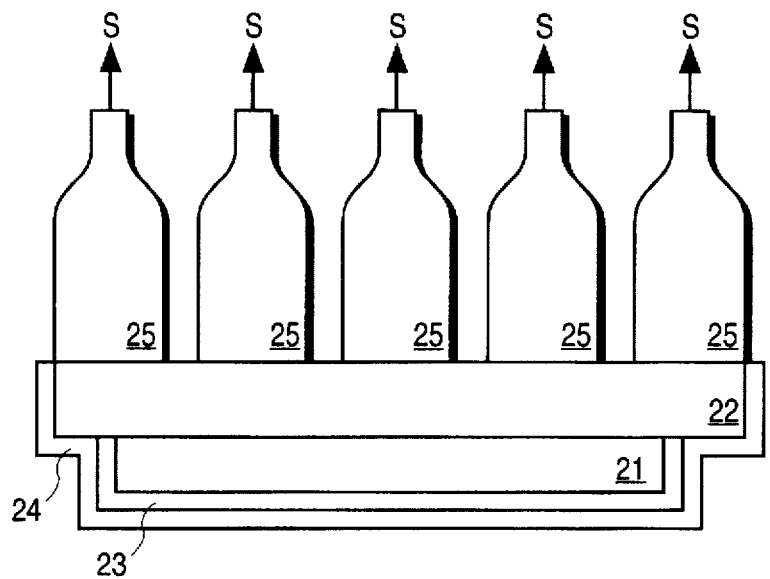
FIG. 2 illustrates a cross-sectional view of a scintillation detector.

FIG. 2 illustrates a cross-sectional view of a detector head which may be used in a nuclear medicine imaging system, such as that shown in FIG. 1. Note however, that the present invention is not limited to use in nuclear medicine. In FIG. 2, the detector head includes a scintillation crystal 21 sandwiched between a layer of aluminum sheet metal 24, which is in contact with the top surface of the crystal 21, and a Pyrex glass plate 22, which is in contact with the bottom (gamma ray entrance) surface of the crystal. The aluminum sheet metal 24 serves to provide a light and moisture barrier and to give mechanical rigidity to the glass-scintillator-aluminum "sandwich". Light from scintillation events exits the crystal at the top surface of the crystal. In contact with the bottom surface of the crystal 21 and inside the aluminum layer 24 is a reflective surface 23, which is designed to cause diffuse reflection of light emitted from within the crystal 21. The reflective surface 23 may be a coating, a layer of reflective paper, or any other form of diffuse reflective surface applied to the bottom surface of the crystal. The layer of aluminum sheet metal 24 partially encases the combination of the crystal 21, the glass plate 22, and the reflective surface 23.

Figure 3:
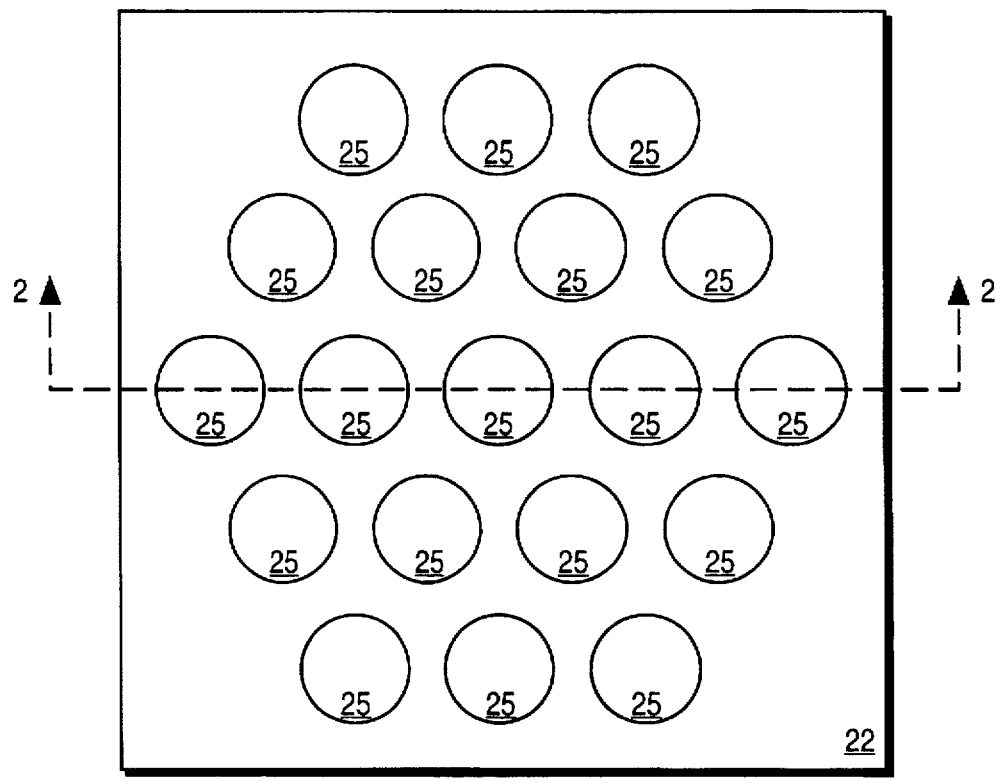
FIG. 3 illustrates a top view of a scintillation detector.

Mounted on a top surface of the glass plate 22, which is not covered by the sheet metal 24, are a number of PMTs 25. The PMTs 25 receive light emitted from scintillation events occurring within the crystal 21 and convert the received light into the electrical signals S that are provided to the position logic 40. FIG. 3 shows a top view of the detector head 20. In FIG. 3, the PMTs 25 are arranged in a hexagonal array on the top surface of the glass plate 22. It should be noted, however, that other geometric arrangements may be used.

Figure 4:
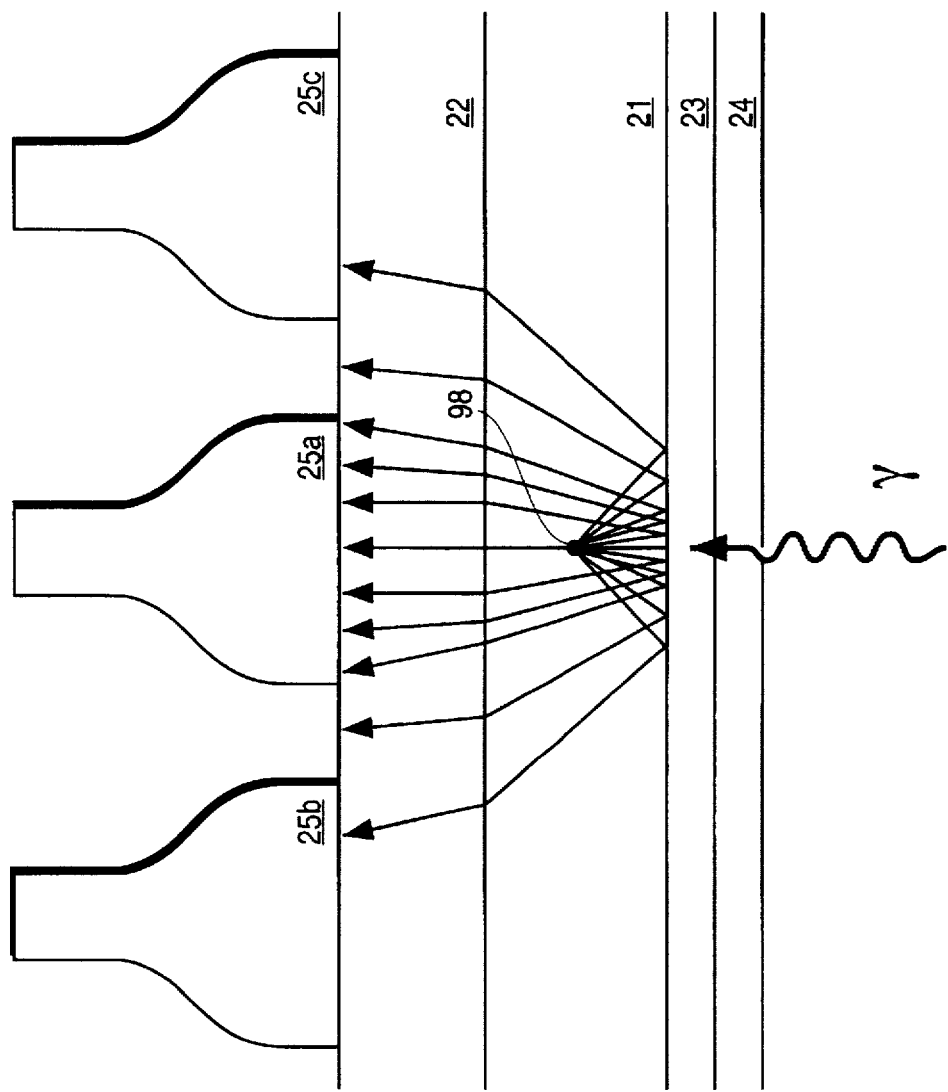
FIG. 4 shows a cross-sectional view of a scintillation detector in which diffuse reflection of light occurs.

For purposes of this description, the PMT which is closest to a given scintillation event shall be referred to as the "peak PMT". Referring still to FIG. 2, assume a scintillation event occurs directly beneath the peak PMT. In that case, some of the light from the event is emitted toward and then reflected by reflective surface 23. However, of the light that is reflected by reflective surface 23, much more of that light gets reflected toward the peak PMT than toward any of the other PMTs. This effect, which is illustrated in FIG. 4, is a result of the diffuse reflective properties of the reflective surface 23. In a typical detector, approximately 50 percent of the total light from the event will enter the peak PMT, whereas approximately 10 percent of the light will enter each of the immediately surrounding PMTs. Such unbalanced light distribution causes inaccuracies in the calculation of position information, which results in spatial resolution modulation.

In FIG. 4, light is emitted from a location 98 at which a scintillation event occurs within the crystal 21. The location 98 of the scintillation event is directly under PMT 25A, the peak PMT. The light is emitted isotropically, although FIG. 4 only shows light rays that are emitted toward the reflective surface 23. The diffuse reflective surface 23 causes much more of the light which it reflects to enter PMT 25A (directly over the location 98 of the scintillation event) than any of the neighboring PMTs, such as PMTs 25B and 25C.

Figure 5A:
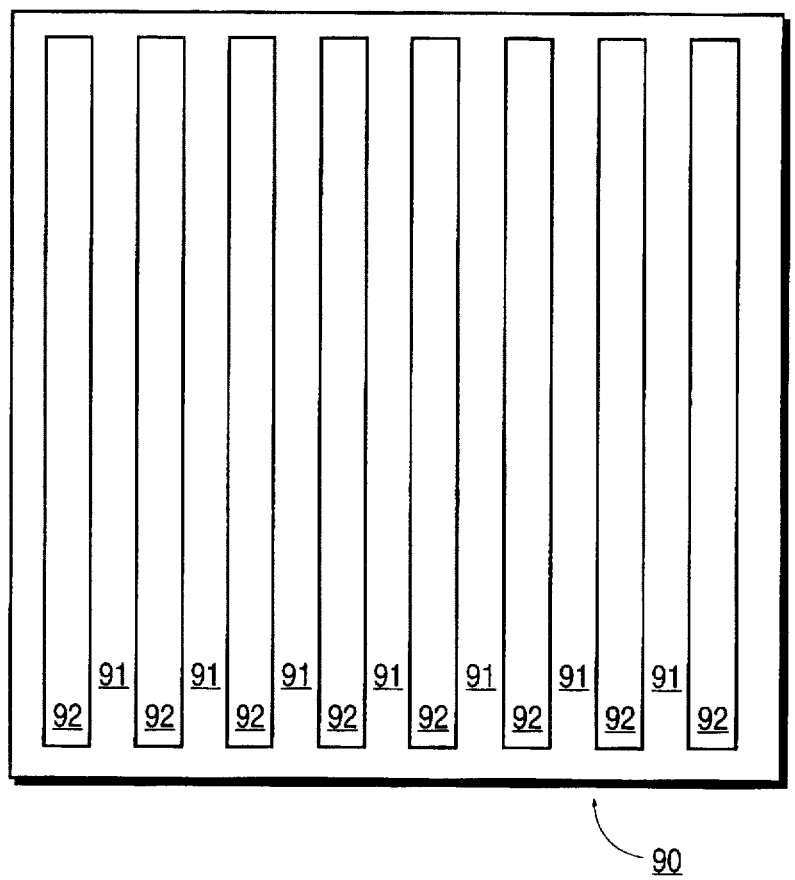
FIG. 5A illustrates a slit phantom used in measuring spatial resolution of a gamma camera.
Figure 5B:
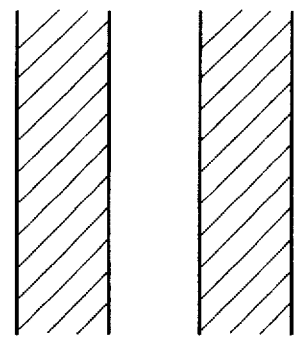
FIG. 5B illustrates an image pattern generated from a slit phantom by a gamma camera having no spatial resolution modulation.
Figure 5C:
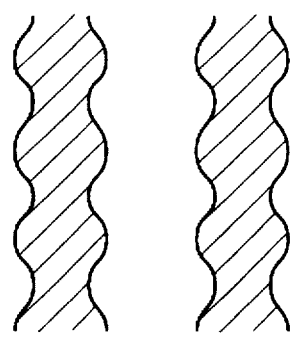
FIG. 5C illustrates an image pattern generated from a slit phantom by a gamma camera which has spatial resolution modulation.

The impact of spatial resolution modulation is described now with reference to FIGS. 5A through 5C. FIG. 5A illustrates a bar phantom 90 which is used in measuring the spatial resolution of a scintillation camera. The bar phantom 90 includes lead strips 91 separated by spaces 92. The lead strips 91 have widths equal to the widths of the spaces 92 between them. During measurement of the spatial resolution, the bar phantom 90 is placed between the detector head and a line or point source of gamma radiation. An image is obtained which, in a camera having no spatial resolution modulation, would appear as in FIG. 5B. In FIG. 5B, the image lines produced by the bar phantom are essentially straight. However, a camera which uses a diffuse reflective surface tends to have resolution modulation, the effect of which is visible as wavy lines in the image of FIG. 5C.

The present invention includes an optical interface which can be used to reduce spatial resolution modulation and to improve gamma camera performance in various other ways. The optical interface is "tailored", in that it has properties which cause it to preferentially reflect and/or transmit light in a designed way. That is, the angle of reflection or transmission of light impinging upon the tailored optical interface is predetermined for a given angle of incidence.

Each point on the optical interface may have reflectance and/or transmission properties that are defined in terms of ranges of angles of incidence of impinging light, i.e., each point is angular-multiplexed. More specifically, for each point on the optical interface, the angle of reflectance or transmission (whichever is applicable) can be made constant for a specified range of angles of incidence. For example, the reflection properties of a given point on the optical interface may be defined as follows: for $0° \leq \theta_I \leq 30°$, $\theta_R = X°$; for $30° \leq \theta_I \leq 60°$, $\theta_R = Y°$; for $60° \leq \theta_I \leq 90°$; $\theta_R = Z°$, where $\theta_I$ represents the angle of incidence, $\theta_R$ represents the angle of reflectance or transmission, and where X, Y, and Z represent numerical constants. Note that these ranges are used only for purposes of illustration. The reflectance and/or transmission properties may vary with location on the optical interface. Thus, the optical interface can be designed so that light distribution into the PMTs is relatively uniform under all conditions, if desired.

The optical interface can be embodied as a reflector coupled to the bottom surface of the scintillation crystal (i.e., the surface closest to the radiation source) and is tailored to reflect light back toward the PMTs in a desired way. Alternatively, the optical interface can be embodied as an optical conductor coupled to the top surface of the scintillation crystal which transmits (redirects) light toward the PMTs in a desired way. Either one or both of these two embodiments may be used in a given scintillation detector. Note that the specific details of the optical interface's reflectance and/or transmission properties will depend upon various factors, such as the purpose for which the interface is to be used and the imaging device in which it will be used.

In one embodiment, the optical interface of the present invention is a diffraction grating. A suitable diffraction grating is a holographic optical element (HOE), which may be either reflective or (optically) transmissive. The diffraction grating may be an integral part of an otherwise conventional reflective surface, such as reflective surface 23 in FIG. 4. For example, if reflective paper is used as the reflective surface 23, appropriately-designed HOEs may be printed, embossed, or otherwise integrated with the reflective paper at selected locations. Alternatively, HOEs or other diffraction gratings may be manufactured separately from a conventional reflective surface and then subsequently affixed to the conventional reflective surface with an appropriate adhesive.

Figure 6A:
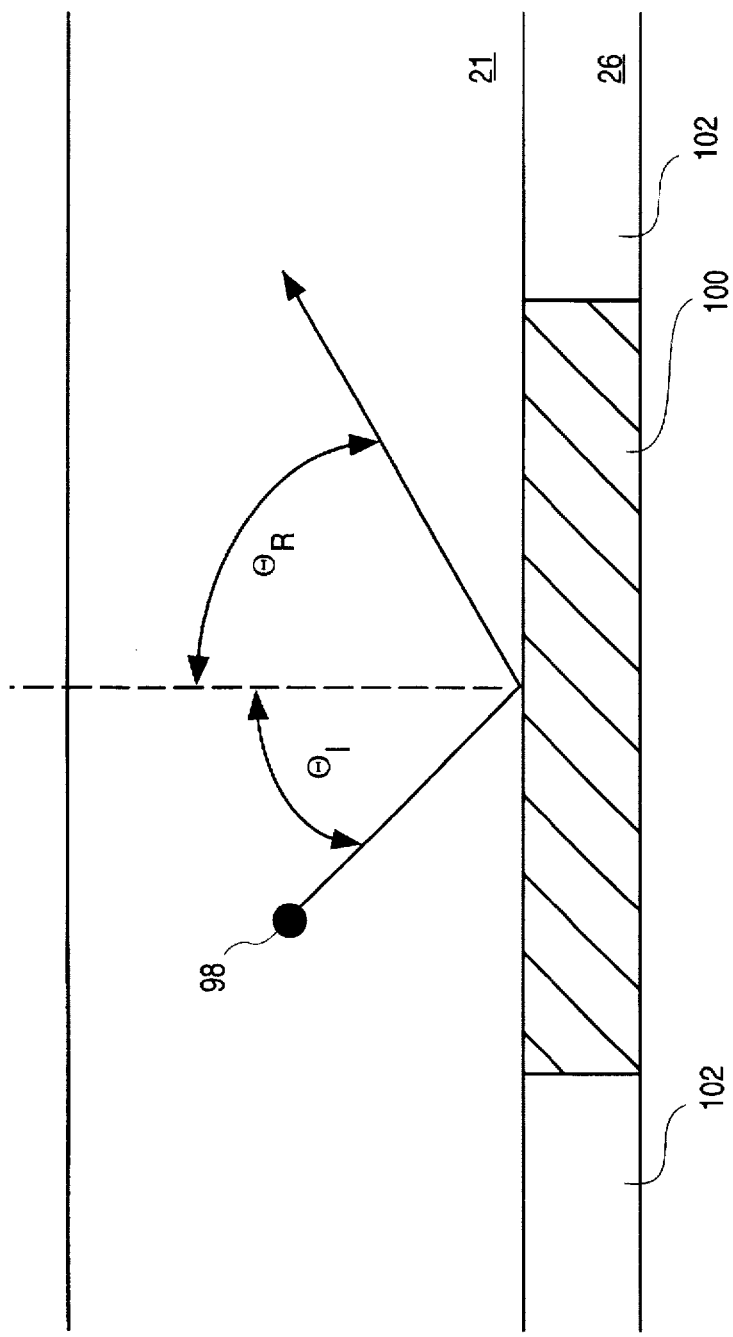
FIG. 6A shows preferential reflection of light by an optical interface, such that the angle of reflection is greater than the angle of incidence.
Figure 6B:
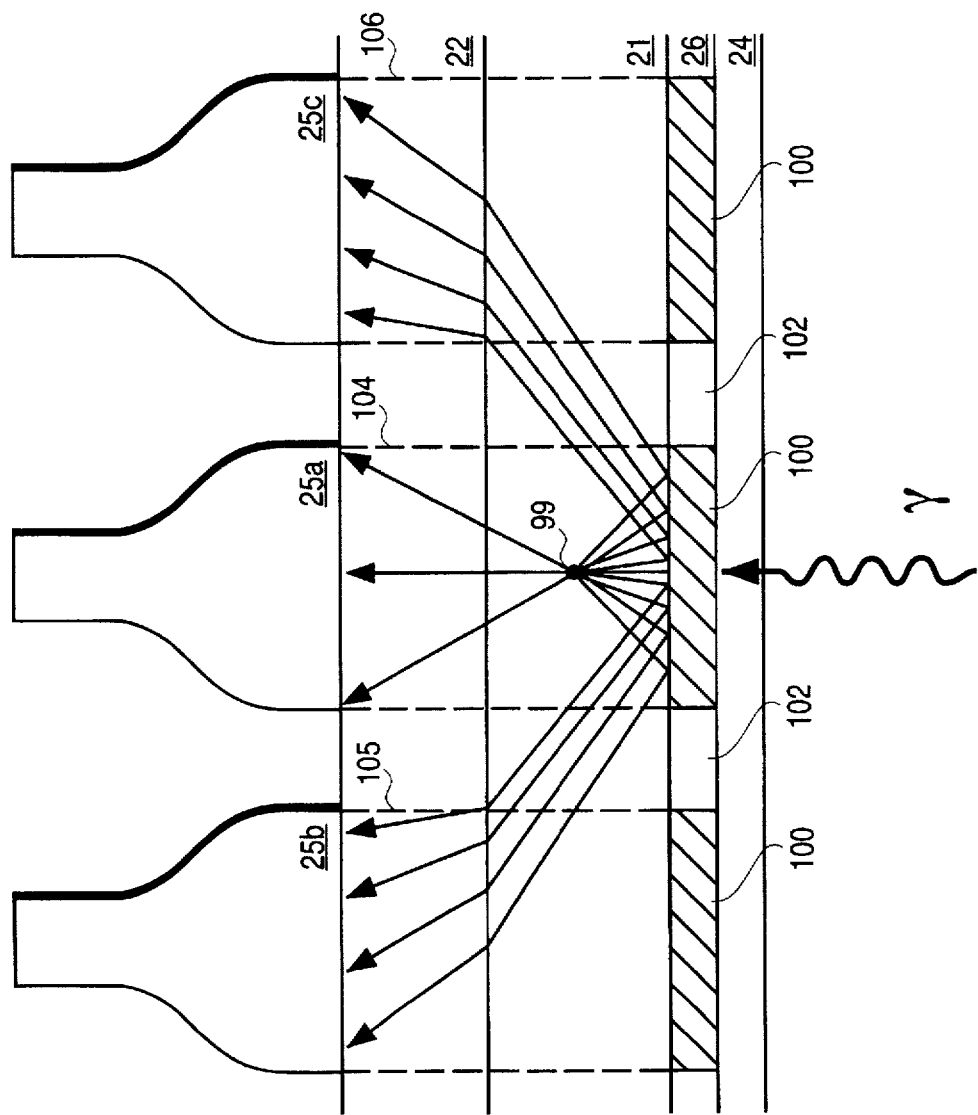
FIG. 6B illustrates a cross section of a scintillation detector in which light is preferentially reflected toward PMTs surrounding the peak PMT.

FIGS. 6A and 6B illustrate one embodiment of the present invention in which the optical interface is a tailored reflector 26. In this embodiment, the tailored reflector 26 is designed so that a light ray impinging upon the tailored reflector 26 in an area 100 located directly under a PMT at a given angle of incidence $\theta_I$ is reflected at a predetermined angle of reflection $\theta_R$, such that the angle of reflection $\theta_R$ is greater than the angle of incidence $\theta_I$ (FIG. 6A). However, the tailored reflector 26 has diffuse reflective properties in areas 102 located under the intersections of PMTs (FIG. 6B). According to the present invention, in contrast with the embodiment of FIG. 4, more of the light emitted from a given scintillation event is reflected toward the PMTs surrounding the peak PMT than toward the peak PMT. For example, in FIG. 6B a scintillation event occurs at a location 99 directly within the view 104 of (i.e., directly under) PMT 25A, the peak PMT. The event does not occur directly within the view 105 of PMT 25B or directly within the view 106 of PMT 25C. The tailored reflector 26, however, preferentially reflects more of the light from the event toward the surrounding PMTs 25B and 25C than toward PMT 25A. Note that it may be desirable to direct light from an event only to the PMTs immediately adjacent to the peak PMT, as will be discussed below.

In the embodiment of FIG. 6B, the tailored optical interface includes distinct areas of diffraction grating 100 (e.g., corresponding to the PMT locations), each of which approximately corresponds in size to the diameter of a PMT. The diffraction gratings in this case are separated by areas 102 having diffuse (or otherwise different) reflective properties, as noted above. However, the tailored reflector may alternatively comprise a larger, continuous diffraction grating having an area that covers a number of PMTs. In that case, the reflective properties of the diffraction grating will be a function of location.

The present invention also has use beyond reducing resolution modulation, as noted above. For example, it would be desirable to have a continuous-crystal scintillation detector which has certain optical properties associated with a block detector. A block detector is characterized by cuts in the scintillation crystal, which form light barriers. As a result, light rays from a given scintillation event tend to be confined within a very small area of the crystal. Such isolation of scintillation events is advantageous, because a large number of events can be processed in parallel with relatively little ambiguity in position determination.

Figure 7:
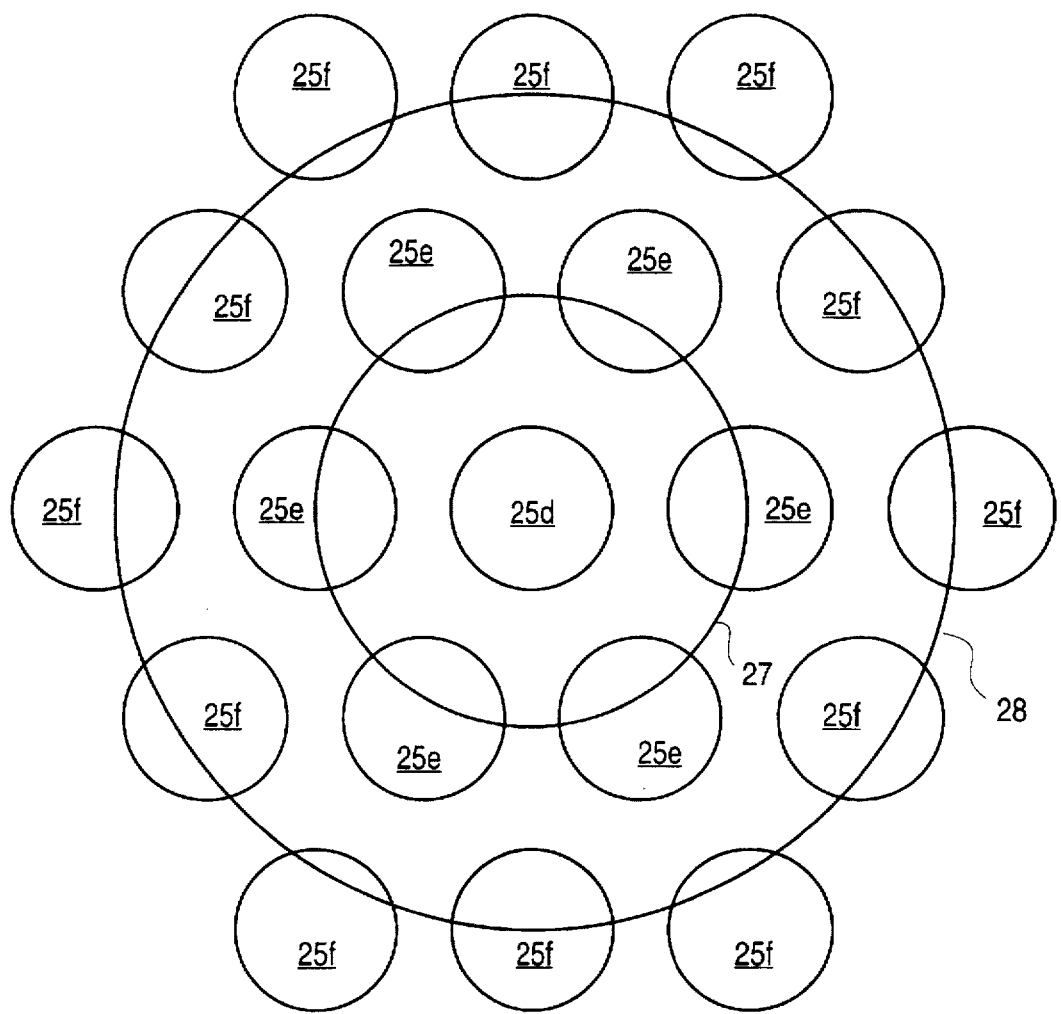
FIG. 7 illustrates an array of photomultipliers arranged in concentric circles around a peak photomultiplier.

Accordingly, a tailored optical interface can be used in conjunction with a continuous-crystal detector to provide increased confinement of light rays, thus giving the continuous-crystal detector some of the properties of a block detector. For example, the present invention can be used to redirect light from an event only to those PMTs immediately adjacent to the peak PMT, but away from PMTs which are farther from the event than the adjacent PMTs. Note that in many PMT arrays, the PMTs are arranged in concentric rings around a given PMT. Referring to FIG. 7, PMTs 25e are arranged in a first (inner) ring 27 centered around PMT 25d, while PMTs 25f are arranged in a second (outer) ring 28 centered around PMT 25d. Assuming PMT 25d is the peak PMT for a given scintillation event, it may be desirable to use a tailored optical interface to direct some of the light from that event toward the PMTs 25e of the inner ring 27, away from PMT 25d. However, it may also be desirable to confine the redirected light to the PMTs 25e of inner ring 27, so that little or none of the light from the event is detected by the PMTs 25f of the outer ring 28. The tailored optical interface can be used to provide such confinement.

Note that by using the optical interface in the above-described manner to confine light rays within a smaller area, an improvement can also be achieved in the trade-off between resolution and stopping power. Generally, spatial resolution is inversely proportional to crystal thickness for a given scintillation material. The reason for this effect is that, in a crystal of a given thickness, light rays from certain events will spread out over a wider area before reaching the PMTs than they would in a crystal that is thinner. However, greater thickness generally provides greater stopping power. Hence, by using the present invention to provide greater confinement of light rays, one can improve the resolution that is achievable with a crystal of a given thickness or use a crystal of greater thickness than could otherwise be used, given some minimum resolution requirement.

Figure 8:
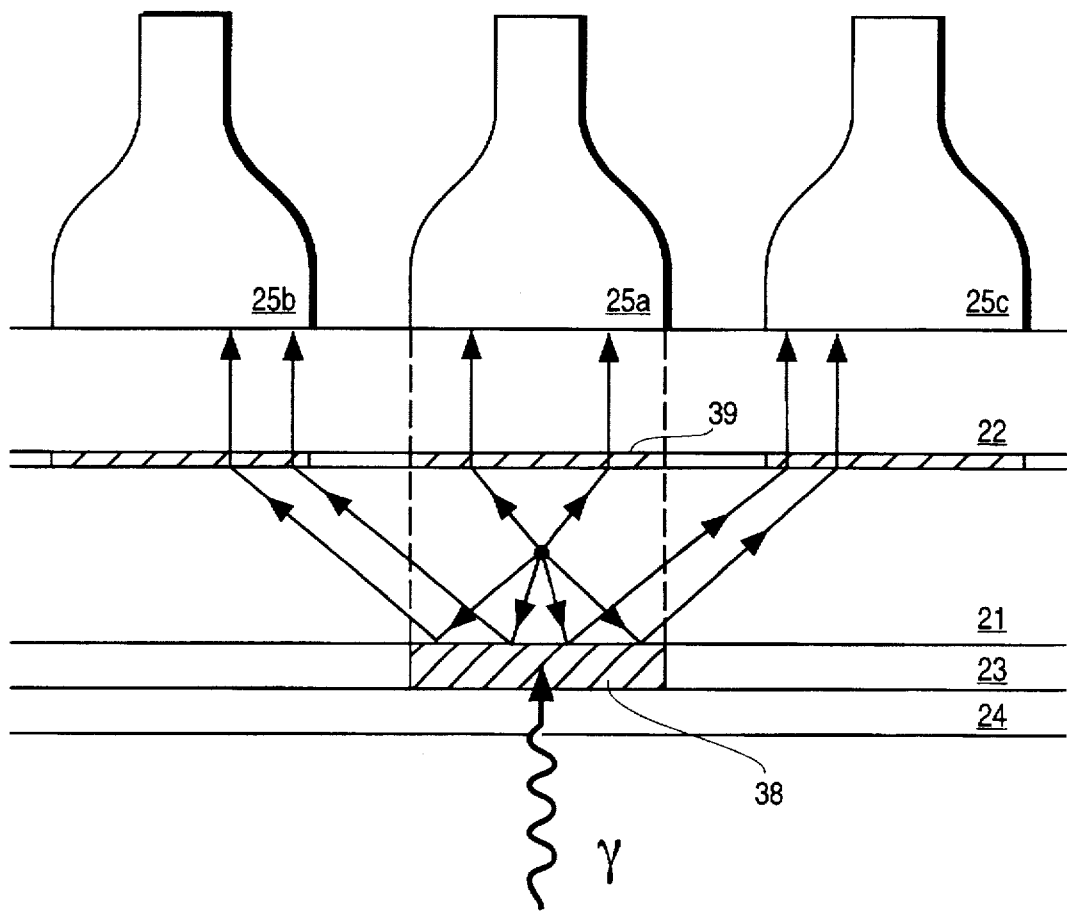
FIG. 8 illustrates a scintillation detector in which a tailored optical conductor is used in conjunction with a tailored optical reflector.

Referring to FIG. 8, a second tailored optical interface, such as a tailored optical conductor 39, may be used in conjunction with a tailored 25 reflector 38 to achieve improved performance. As noted above, the optical interface in this embodiment may have distinct areas of diffraction grating corresponding to the locations of individual PMTs or a larger, continuous diffraction grating covering the views of several PMTs.

Figure 9:
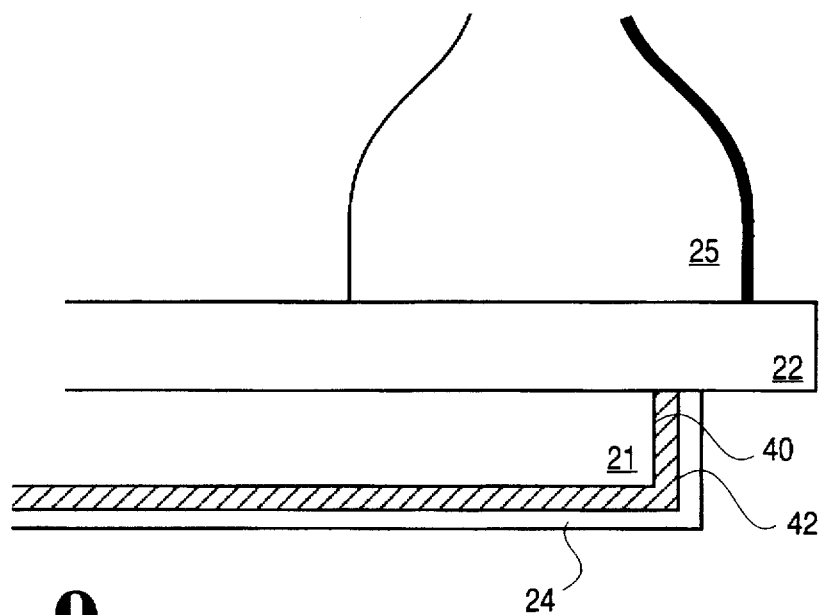
FIG. 9 illustrates a scintillation detector which includes a diffraction surface optically coupled to an edge of the scintillator.

Reflectance tailoring according to the present invention can also be applied to the edges of the crystal 21 where light tends to be trapped, as shown in FIG. 9. In that case, the light can be preferentially directed toward PMTs located away from the edges of the crystal. In FIG. 9, a tailored reflector 42 is coupled to both the bottom surface and to the edge 40 of the crystal 21.

Figure 10:
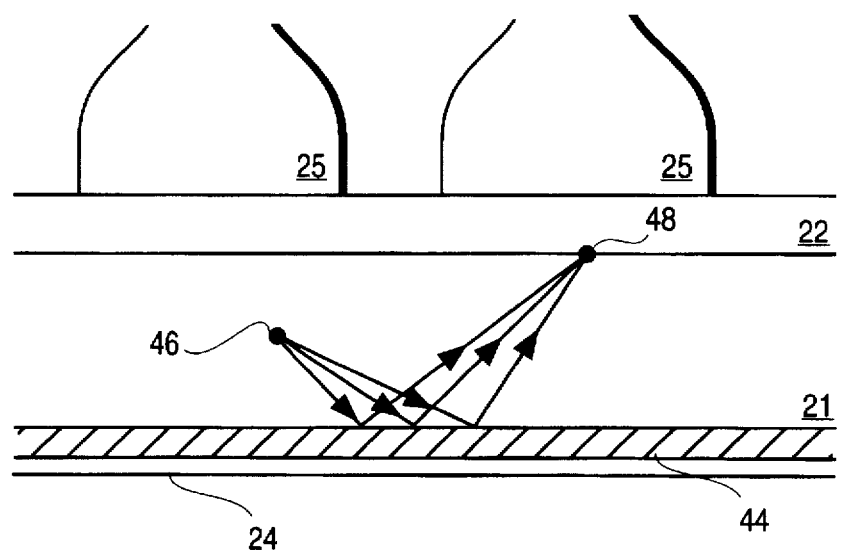
FIG. 10 illustrates a tailored reflector which focuses reflected light rays on a single point.
Figure 11:
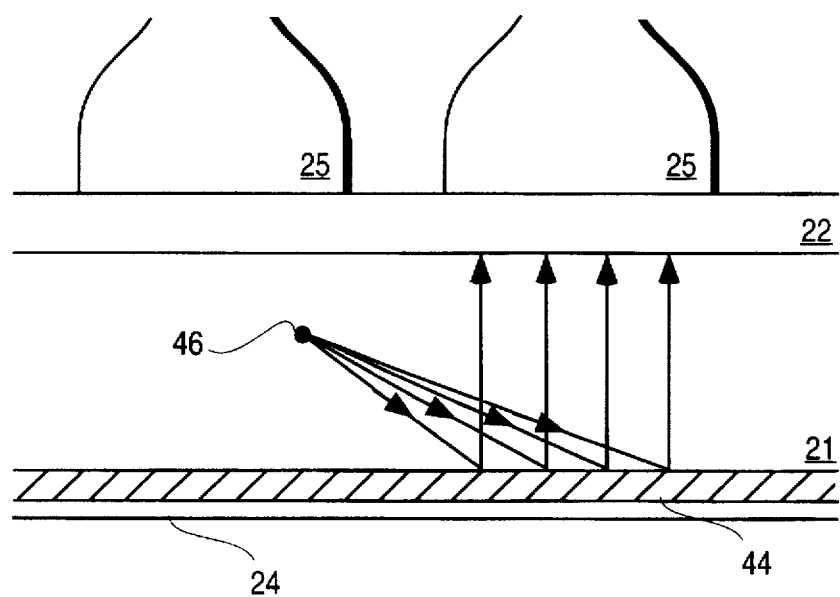
FIG. 11 illustrates a tailored reflector which reflects light rays impinging on the reflector from different angles in a direction perpendicular to the reflector.

It may be desirable to design the optical interface to focus light on a single point. Thus, as shown in FIG. 10, light emitted at various angles from a given scintillation event 46 is reflected by tailored reflector 44 and focused at a particular point 48, such as a point directly under the center of a PMT. Alternatively, it may be desirable to reflect light rays which impinge on the reflector 44 at any angle of incidence within a predetermined range in a direction perpendicular to the reflector 44 (i.e., directly up toward a PMT), as shown in FIG. 11.

Hence, the present invention can be used to reduce spatial resolution modulation caused by non-uniform light reflectance and PMT light collection. Further, the present invention can be used to give a continuous-crystal scintillator certain optical properties of a block detector, or to alter the optical properties of a scintillation crystal to resemble those of a thinner crystal.

Thus, although the present invention has been described with reference to specific exemplary embodiments, it will be evident that various modifications and changes may be made to these embodiments without departing from the broader spirit and scope of the invention as set forth in the claims. Accordingly, the specification and drawings are to be regarded in an illustrative rather than a restrictive sense.

What is claimed is:

1. A scintillation detector comprising:
   a scintillator;
   a plurality of light detectors optically coupled to the scintillator; and
   an optical interface comprising a diffraction grating optically coupled to the scintillator, such that light emitted from within the scintillator impinges upon a point on the diffraction grating, wherein the diffraction grating preferentially steers the light toward a predetermined subset of the light detectors, wherein the predetermined subset is based on the location of the point.

2. A scintillation detector of claim 1, wherein the diffraction interface is reflective, and wherein light impinging upon the diffraction interface at any of a plurality of different angles of incidence is reflected in a direction perpendicular to the diffraction interface.

3. A scintillation detector according to claim 1, wherein the diffraction grating comprises a holographic element.

4. A scintillation detector according to claim 1, wherein the optical interface is reflective.

5. A scintillation detector according to claim 1, wherein the optical interface is optically transmissive.

6. A scintillation detector according to claim 1, wherein the scintillator comprises a top surface optically coupled to the light detectors and a bottom surface substantially parallel to the top surface, wherein the scintillator further comprises a plurality of edges substantially perpendicular to the top and bottom surfaces, and wherein the optical interface is a reflector coupled to one of the edges.

7. A scintillation detector according to claim 1, wherein the plurality of light detectors comprises a first light detector and a first plurality of light detectors adjacent to the first light detector, and wherein the optical interface receives light emitted from a point within the scintillator that is directly within a view of the first light detector and not directly within a view of any of the first plurality of light detectors, and wherein a portion of the light is preferentially directed by the optical interface away from the first light detector and toward the first plurality of light detectors.

8. A scintillation detector according to claim 7, wherein said portion of the light is further directed by the optical interface so that said portion of the light is confined within view of the first light detector and the first plurality of light detectors.

9. A scintillation detector according to claim 1, wherein light emitted from within the scintillator impinges upon the optical interface at an angle of incidence, and wherein the optical interface reflects the light at a predefined angle of reflection that is greater than the angle of incidence.

10. A scintillation detector according to claim 1, wherein the plurality of light detectors comprises a first light detector and a plurality of light detectors surrounding the first light detector, and wherein the optical interface receives light emitted from a point within the scintillator that is directly within view of the first light detector and not directly within a view of any of the surrounding light detectors, and wherein the optical interface preferentially directs some of the light toward the plurality of light detectors surrounding the first light detector, wherein light emitted from within the scintillator impinges upon the optical interface at an angle of incidence, and wherein the optical interface reflects the light at a predefined angle of reflection that is less than the angle of incidence.

11. A scintillation detector according to claim 1, wherein light can impinge upon the point on the optical interface at a plurality of angles of incidence, and wherein the optical interface reflects the light impinging on the point from any of the angles of incidence at a single, predetermined angle of reflection.

12. A scintillation detector of claim 1, wherein the diffraction interface is reflective, and wherein light impinging upon the diffraction interface at any of a plurality of different angles of incidence is reflected to a single point.

13. A scintillation detector comprising:
   a scintillation crystal;
   a plurality of photomultipliers optically coupled to the scintillation crystal;
   an optical conductor optically coupled between the scintillation crystal and the photomultipliers; and
   a diffraction interface optically coupled to the scintillation crystal, wherein the diffraction interface redirects light emitted from a scintillation event within the scintillation crystal toward a predetermined subset of the photomultipliers, wherein the predetermined subset is a function of a location of the scintillation event.

14. A scintillation detector according to claim 13, wherein the diffraction interface comprises a holographic optical element.

15. A scintillation detector according to claim 13, wherein the scintillation detector has a top surface coupled to the optical conductor and a bottom surface substantially parallel to the top surface, and wherein the diffraction interface is a reflective interface coupled to the bottom surface.

16. A scintillation detector according to claim 15, wherein the diffraction interface redirects the light toward the predetermined subset of the photomultipliers in a direction perpendicular to the optical conductor.

17. A scintillation detector according to claim 13, wherein the scintillation detector has a top surface coupled to the optical conductor, and wherein the diffraction interface is an optically transmissive interface coupled to the top surface, such that light emitted within the scintillation crystal is conducted through the diffraction interface to the optical conductor.

18. A scintillation detector according to claim 13, wherein the scintillation crystal comprises a top surface optically coupled to the photomultipliers and a bottom surface substantially parallel to the top surface, wherein the scintillation crystal further comprises a plurality of edges substantially perpendicular to the top and bottom surfaces, and wherein the diffraction interface is a reflective interface coupled to the edges.

19. A scintillation detector according to claim 13, wherein the subset is a peak photomultiplier with respect to the scintillation event.

20. A scintillation detector according to claim 13, wherein the plurality of photomultipliers comprises a peak photomultiplier with respect to the scintillation event, and wherein the subset is one or more photomultipliers other than the peak photomultiplier.

21. A scintillation detector according to claim 13, wherein light emitted from within the scintillation crystal impinges upon the diffraction interface at an angle of incidence, and wherein the diffraction interface reflects the light at a predetermined angle of reflection that is greater than the angle of incidence.

22. A scintillation detector according to claim 13, wherein light emitted from within the scintillation crystal impinges upon the diffraction interface at an angle of incidence, and wherein the diffraction interface reflects the light at a predetermined angle of reflection that is less than the angle of incidence.

23. A scintillation detector according to claim 13, wherein light can impinge upon a point on the diffraction interface at any of a plurality of angles of incidence, and wherein the diffraction interface reflects the light impinging on the point from any of the plurality of angles of incidence at a single, predetermined angle of reflection.

24. A scintillation camera detector head comprising:
   a scintillation crystal;
   a plurality of light detectors optically coupled to the scintillation crystal; and
   a reflective surface optically coupled to the scintillation crystal, the reflective surface reflecting light impinging upon the surface at a given angle of incidence at a predetermined angle of reflection, such that light emitted from a location within the scintillation crystal directly under a first one of the light detectors is preferentially reflected toward one or more of the light detectors other than the first one of the light detectors.

25. The scintillation camera detector head of claim 24, wherein the reflective surface comprises a diffraction surface.

26. The scintillation camera detector head of claim 25, wherein the diffraction surface comprises a holographic optical element.

27. A scintillation camera detector head of claim 24, wherein light impinging upon the diffraction interface at any of a plurality of angles of incidence is reflected to a single point.

28. A scintillation camera detector head of claim 24, wherein light impinging upon the diffraction interface at any of a plurality of angles of incidence is reflected in a direction perpendicular to the diffraction interface.

29. In a scintillation detector including a scintillator optically coupled to a plurality of light detectors, a method of distributing light from a scintillation event occurring within the scintillator, the method comprising redirecting some of the light from the event which impinges on a surface toward a predetermined subset of the light detectors based on an angle of incidence of the light with respect to the surface.

30. A method according to claim 23, wherein said redirecting comprises preferentially directing some of the light from the event away from a peak light detector.

31. A method according to claim 30, wherein said redirecting comprises preferentially reflecting the light from the event away from the peak light detector.

32. A method according to claim 26, wherein said redirecting comprises preferentially conducting the light from the event away from the peak light detector.

33. A method according to claim 33, wherein said redirecting comprises preferentially directing the light from the event toward a peak light detector.

34. A method according to claim 33, wherein said redirecting comprises preferentially reflecting the light from the event toward the peak light detector.

35. A method according to claim 33, wherein said redirecting comprises preferentially conducting the light from the event toward the peak light detector.

36. In a nuclear medicine scintillation detector including a scintillator optically coupled to a plurality of light detectors, a method of controlling the distribution of light from a scintillation event within the scintillator, the method comprising:

receiving light from the scintillation event; and preferentially reflecting the light toward a predetermined subset of the light detectors, such that the predetermined subset is dependent upon a location of the event within the scintillator.

37. A method according to claim 36, wherein said reflecting comprises preferentially reflecting the light from the event away from a peak light detector.

38. A method according to claim 36, wherein said reflecting comprises preferentially reflecting the light from the event toward a peak light detector.

39. An apparatus for use in a radiation detector, the radiation detector of the type having light detectors for detecting scintillation events, the apparatus comprising:

a scintillator; and a diffraction interface optically coupled to the scintillator, such that light emitted from within the scintillator impinges upon a point on the diffraction interface, wherein the diffraction interface preferentially steers the light toward a predetermined subset of the light detectors, wherein the predetermined subset is based on the location of the point.

40. An apparatus according to claim 39, wherein light emitted from within the scintillator impinges upon the diffraction interface at an angle of incidence, and wherein the diffraction interface reflects light at a predefined angle of reflection that is greater than the angle of incidence.

41. An apparatus according to claim 39, wherein the diffraction interface comprises a holographic optical element.

42. An apparatus according to claim 41, wherein the diffraction interface is reflective.

43. An apparatus according to claim 39, wherein the diffraction interface is optically transmissive.

44. A scintillation detector comprising:

a scintillator;

a plurality of light detectors optically coupled to the scintillator; and an optical interface optically coupled to the scintillator, the optical interface such that a plurality of light rays emitted within the scintillator and impinging upon the optical interface from a plurality of different incident angles are each redirected by the optical interface toward the light detectors at the same angle.

45. A scintillation detector according to claim 44, wherein the optical interface is a diffraction grating.

46. An scintillation detector according to claim 44, wherein the diffraction grating is a holographic optical element.

47. A scintillation detector according to claim 44, wherein the plurality of different incident angles comprise a plurality of acute angles relative to the optical interface, the optical interface redirecting each of the plurality of light rays perpendicular to the optical interface.

48. A scintillation detector according to claim 44 wherein the optical interface is reflective, the optical interface reflecting each of the light rays toward the light detectors at said same angle.

49. A scintillation detector according to claim 44, wherein the optical interface is transmissive, the optical interface transmitting each of the light rays toward the light detectors at said same angle.

* * * * *